US009171445B2

(12) United States Patent
Nishihara et al.

(10) Patent No.: US 9,171,445 B2
(45) Date of Patent: Oct. 27, 2015

(54) ACTIVITY LEVEL MONITORING PARTICIPANT STATION NETWORK

(71) Applicants: H Keith Nishihara, Los Altos, CA (US); Neil D. Hunt, Los Altos, CA (US); Catherine Lu, Los Altos, CA (US); Julie Raymond, Los Altos, CA (US)

(72) Inventors: H Keith Nishihara, Los Altos, CA (US); Neil D. Hunt, Los Altos, CA (US); Catherine Lu, Los Altos, CA (US); Julie Raymond, Los Altos, CA (US)

( * ) Notice: Subject to any disclaimer, the term of this patent is extended or adjusted under 35 U.S.C. 154(b) by 0 days.

(21) Appl. No.: 14/574,369

(22) Filed: Dec. 17, 2014

(65) Prior Publication Data

US 2015/0179040 A1 Jun. 25, 2015

Related U.S. Application Data

(60) Provisional application No. 61/920,629, filed on Dec. 24, 2013.

(51) Int. Cl.
*G08B 21/04* (2006.01)
*H04L 29/08* (2006.01)
*H04M 1/725* (2006.01)
*H04W 4/04* (2009.01)

(52) U.S. Cl.
CPC .......... *G08B 21/0415* (2013.01); *H04L 67/12* (2013.01); *H04M 1/72538* (2013.01); *H04W 4/043* (2013.01); *A61M 2230/63* (2013.01)

(58) Field of Classification Search
CPC .. G08B 21/04; G08B 21/0423; G08B 25/016; G08B 21/0415; H04L 67/12; H04M 1/72538; H04W 4/043
USPC ............... 340/539.2, 573.1; 379/38
See application file for complete search history.

(56) References Cited

U.S. PATENT DOCUMENTS

| | | | |
|---|---|---|---|
| 4,284,849 A | 8/1981 | Anderson | |
| 6,696,957 B2 | 2/2004 | Shepher | |
| 6,856,249 B2 | 2/2005 | Strubbe | |
| 6,856,807 B1* | 2/2005 | Raith | 455/456.1 |
| 7,138,902 B2 | 11/2006 | Menard | |
| 7,336,166 B2 | 2/2008 | Akamatsu | |
| 8,081,082 B2 | 12/2011 | Malik | |
| 8,199,008 B2 | 6/2012 | Yang | |
| 8,589,174 B2 | 11/2013 | Nelson | |
| 2006/0223518 A1* | 10/2006 | Haney | 455/420 |
| 2009/0251312 A1* | 10/2009 | Shelton et al. | 340/539.13 |
| 2009/0278738 A1* | 11/2009 | Gopinath | 342/357.12 |
| 2009/0322540 A1* | 12/2009 | Richardson et al. | 340/573.7 |
| 2010/0160004 A1* | 6/2010 | Alameh et al. | 455/575.1 |
| 2010/0167792 A1* | 7/2010 | Chen et al. | 455/566 |
| 2012/0161969 A1* | 6/2012 | Husen et al. | 340/573.1 |
| 2012/0290311 A1* | 11/2012 | Tara et al. | 705/2 |
| 2013/0040600 A1* | 2/2013 | Reitnour et al. | 455/404.2 |
| 2013/0132028 A1* | 5/2013 | Crankson et al. | 702/160 |
| 2013/0183924 A1* | 7/2013 | Saigh et al. | 455/404.2 |
| 2013/0190008 A1 | 7/2013 | Vathsangam | |
| 2013/0325396 A1* | 12/2013 | Yuen et al. | 702/160 |
| 2014/0114564 A1* | 4/2014 | Callaghan et al. | 701/416 |
| 2014/0253323 A1* | 9/2014 | Berven | 340/539.12 |
| 2014/0266702 A1* | 9/2014 | Forster-Knight | 340/539.13 |
| 2014/0266791 A1 | 9/2014 | Lloyd | |
| 2014/0354527 A1* | 12/2014 | Chen et al. | 345/156 |
| 2014/0368658 A1* | 12/2014 | Costa et al. | 348/158 |

* cited by examiner

*Primary Examiner* — Benjamin C Lee
*Assistant Examiner* — Stephen Burgdorf

(57) ABSTRACT

A network of interreporting participant stations configured to monitor and analyze station movement such that activity levels of the individual stations can be determined and reported across the network to alert participant stations whenever the activity level of any one of the participant stations has dropped to a pre-determined level.

17 Claims, 9 Drawing Sheets

ACTIVITY LEVEL MONITORING PARTICIPANT STATION NETWORK

RELATED APPLICATION

The present application claims priority to U.S. Provisional Patent Application Ser. No. 61/920,629, entitled Mutual Welfare Monitor Network, filed Dec. 24, 2013.

TECHNICAL FIELD

The present invention provides devices, systems and networks allowing groups of individuals to mutually monitor each other's welfare by monitoring each other's activity levels.

BACKGROUND

Persons living alone are at risk of going without help for a long period if they have an accident or medical emergency that leaves them incapacitated. This is especially true for the elderly but the risk exists for anyone who spends long periods alone. One solution to this problem is for members of a family or small group of friends to routinely check up on each other.

At present devices exist to facilitate the health and welfare monitoring of a person living alone. These devices typically incorporate sensors in a living space to track the resident's activity level and can send an alarm to a third party if that activity falls below some threshold. Another variation requires the resident to wear a small button box such as a bracelet or necklace that allows the owner to signal for help. A drawback of the former sensor is the requirement for specially instrumenting the home to support the monitoring. This also limits monitoring to just the instrumented areas. A drawback of the latter is the requirement that the user carry it at all times which is often not practical. Furthermore the user must be capable of activating the alarm in time of need, which is not always possible.

At present all such devices are designed with a subject to be monitored and one or more third parties to be notified if an emergency occurs. Such products are intended primarily for individuals with special needs or higher risk of needing assistance such as the elderly.

In addition, there is a wider demographic of individuals who live alone some or all of the time. Any of these individuals is at risk for a medical emergency such as a heart attack or a fall that could leave them unable to seek help on their own. Typically these individuals would not consider setting up a welfare alerting system for themselves given the low probability of an incident. However, these same individuals typically have a small circle of friends or relatives who would from time to time manually check up on each other as a matter of habit if one of their friends has not been heard from for too long.

Additionally, there is a demographic of people who wish to encourage their friends and associates to remain physically active and to motivate one another to achieve healthy activity and exercise goals. This had traditionally been difficult to do, as it often involves making repetitive inquiries of a personal nature.

SUMMARY OF INVENTION

As a safety system, the present invention builds on the behavior of friends checking up on each other and works to shorten the time to discovery of an incident. It advantageously provides non-intrusive welfare monitoring through sensing capabilities and usage activity on modern mobile devices such as cell phones as well as usage activity on other network connected devices such as laptop computers. The present invention makes this monitoring non-intrusive by only checking for the lack of activity, for example, determining if the monitored device has been physically picked up or moved over a particular monitoring interval of time. Another advantage of the present design is that it operates in the background on enabled mobile devices and preferably attempts to avoid annoying the users with false alarms by requiring a statistically significant absence of activity before generating an alert. It enhances a small social group's ability to detect incidents among its members that require attention. An optional variation of the present invention allows a group to monitor and compare activity scores for each member of the group as a means for encouraging increased activity and for discovering unusual changes in the activity level of a member over time.

The present invention treats welfare monitoring as a symmetric activity among the members of a social group. Each member of the group, such as of friends or relatives, takes on the role of the monitored individual and of the third party who could be notified in case of an emergency. This symmetric design increases the accessibility of welfare monitoring to a wider demographic which includes persons of all ages who at times may be alone for extended periods. Friends or relatives who make up such a welfare monitoring group are able to monitor each other in a non-invasive manner that does not compromise individual privacy.

To be accepted and used continuously, the present invention has a very low overhead for setup and operation. It is installed, enabled and forgotten as it continues to operate as a background process on each user's mobile devices and the system reliably detects emergencies with very low false alarm rates.

In one preferred embodiment, the present invention provides a network of participant stations that are configured to monitor and analyze their own station movement such that activity levels of individual stations can be determined and reported across the network. As such, the present invention preferably comprises a plurality of participant stations, with each participant station comprising: (a) a communication system enabling message transmission to the other participant stations in the network; (b) one or both of: (i) a GPS for determining the location of the participant station, or (ii) a movement sensor for detecting movement of the participant station (e.g.: a user picking up or interacting with the device); (c) a movement recording system that records the change of one or both of the location or movement of the participating station over time; (d) an activity level measuring system that measures an activity level of the participating station over intervals of time based on changes in one or both of the location or movement of the participant station; (e) a movement threshold level identifier that identifies when the station's activity level has remained below a pre-determined threshold for a pre-determined period of time; and (f) an alert system that transmits a message through the communication system to other participant stations in the network when the movement threshold level identifier has determined that the activity level has remained below the pre-determined threshold for the pre-determined period of time.

In another preferred embodiment, the present invention instead uses an activity level reporting system that transmits a message reporting the user's activity level through the communication system to other participant stations. This embodiment of the invention can be used for members of the group to encourage one another to exercise more, rather than as a safety system that warns that one user's activity level is too low.

In yet another embodiment, the present invention provides a computer application resident on a monitored device, comprising: (a) a software module for monitoring physical movement of the monitored device over a period of time; (b) a software module for determining if the amount of physical movement of the monitored device has fallen below a pre-determined threshold for a pre-determined period of time; and (c) a software module for alerting a second device if the physical movement of the monitored device has fallen below the pre-determined threshold for the pre-determined period of time.

Figure 1A:
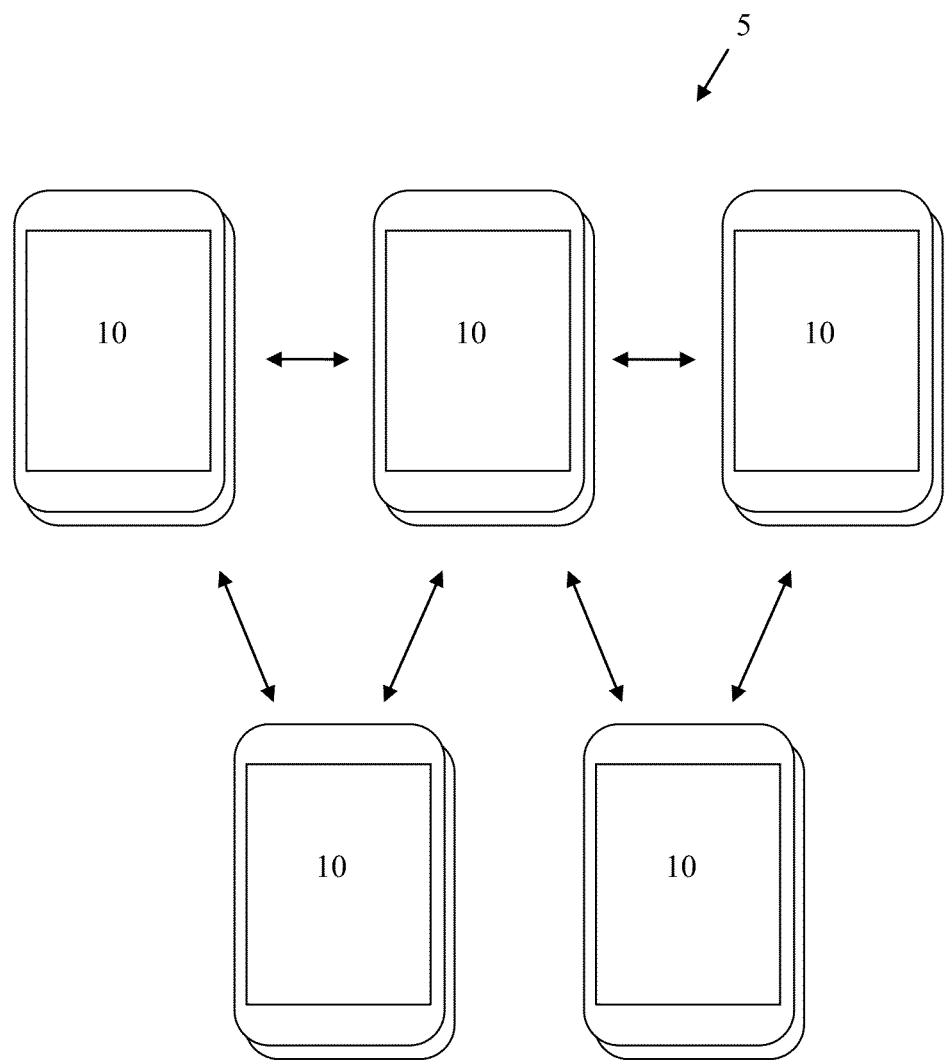
FIG. 1A illustrates a network of interreporting participant stations according to a first embodiment of the present invention.

DETAILED DESCRIPTION OF THE DRAWINGS (a) Overview of System Operation

The present invention provides a network of participating stations that each monitor their own activity levels, and can report their activity levels to one another. Each participant in the network has a monitored device (which may preferably be a smart phone). As will be explained, the present network can be used as a warning system to alert participants that one of their members has a low activity level (and may have had an accident or medical emergency); or the present network can be used as a system for members to encourage one another to accomplish desired exercise goals.

In one preferred embodiment, an application is resident on a monitored smart phone of each member of a mutual welfare monitoring group of individuals. This application's associated physical componentry (which may include a GPS, accelerometers, gyroscopes, communication lines, and power level monitors) together monitor each device's periodic movement (i.e.: its activity level) and checks an activity record periodically to verify that the device has been physically handled during at least some part of a previous interval of time. Preferably, the length of that time interval may be a configurable parameter set to be sufficiently large that the likelihood of no activity for the monitored device is very small. But it is also preferably set to be as short as needed such that the present system can send out an alert message in a timely fashion if the station's activity level remains too low over a pre-determined period of time. In a preferred embodiment, a controlling software application operates as a background process on the monitored device that only wakes periodically throughout the day, communicates with the physical motion and power level sensors, and logs any detected movement since the last awakening. The generated activity log is then checked back over a period of time. This period of time may optionally be set as the past 4 hours during the day. A longer interval can be set at night, taking into account the sleeping schedule of the device's owner. In addition, connecting the device to charge (i.e.: plugging in the cell phone) is a strong signal that indicates that the device is not being carried around, and that the owner may be sleeping. However, if no activity is measured over an extended period of time, an alert sequence can be initiated.

In preferred embodiments, the alert sequence first attempts to get the attention of the device's owner when the activity level is measured to be low. In one preferred embodiment, a spoken voice is generated asking the owner to physically handle the mobile device, and asks if all is well. In another preferred embodiment, a distinctive ring tone is emitted to signal the device's owner that the welfare monitoring system is preparing to send out an alert to other participating stations (i.e.: to other users' monitored smart phones). In a variation of this preferred embodiment, a sequence of ring tones can be used. For example, the first ringtone can be less loud and disrupting, and possibly employs vibration. Subsequent ringtones can get louder and more disruptive to get the attention of the device owner. In addition, some devices (such as the iPhone) may offer bright flashing lights to aid detection by users without their hearing aid. This status check with the owner may continue for several tries over an extended period of time. If no response is detected from the device's owner, the alert sequence then advances to attempting to contact another member of the device owner's mutual welfare monitoring network. In a preferred embodiment, an SMS text message is sent to one or more members of the mutual welfare monitoring network. This text message provides the identity of the sending device's owner, thereby allowing the contacted network member to call or text back to check on the device owner's welfare. In a preferred embodiment, the message also may carry information about the location of the monitored device sending out the alert message. In another preferred embodiment, the alert sequence continues to send alerts to other members of the mutual welfare monitoring network until an acknowledge signal is received from some member of the mutual welfare monitoring group (i.e.: indicating that one member of the network is responsibly checking in on the participant station's owner that has an unusually low activity level).

(b) Network Configuration and Participant Station Physical Components

Figure 1B:
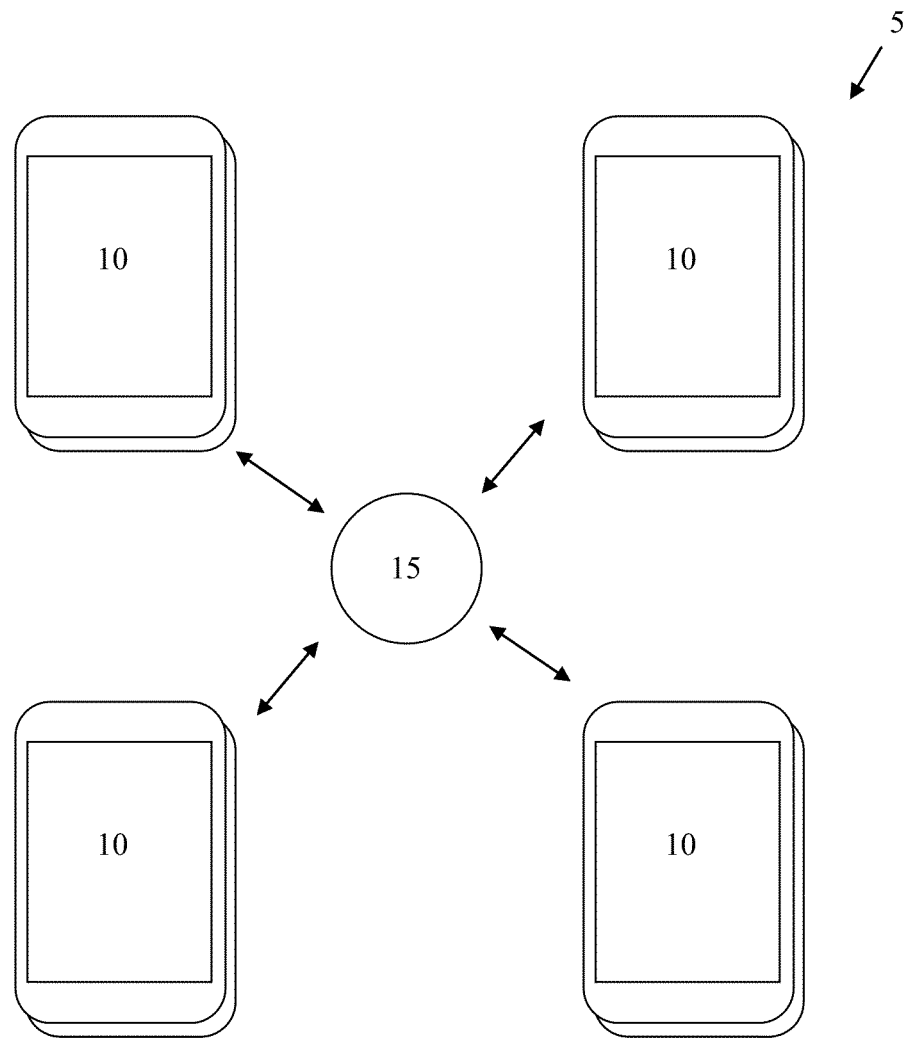
FIG. 1B illustrates a network of interreporting participant stations according to a second embodiment of the present invention.

FIGS. 1A and 1B illustrate two preferred networks of inter-reporting participant stations that alert participants when the activity levels of one of the participant stations falls below a pre-determined level for a pre-determined period of time. These network configurations may be used either as a safety network, or as a system for participants to mutually encourage one another to remain active.

In FIG. 1A, a network 5 of interreporting participant stations (i.e.: monitored devices) 10 is provided. Participant stations 10 may be smart phones, or laptops or any other computerized device (even including toys), provided that the monitored devices are capable of communication to other participant stations in the network. Each participant station 10 has preferred physical components (described in detail in FIG. 2) and is configured to communicate with one another using any method or system of suitable communication including cell phone networks, wi-fi networks, Internet communication systems, etc. In FIG. 1A, network 5 permits all participant stations 10 to communicate directly with one another (for example, a plurality of monitored cell phones 10 communicating by text or voice over a standard cellular network). In one embodiment this peer to peer communication entails use of the mobile device's cellular radio function. An advantage of this architecture is its independence from reliance on a central server.

FIG. 1B is similar, but further adds a central server 15 to network 5. In FIG. 1B, each of participant stations 10 now communicate with and through central server 15. Central server 15 maintains data for each network and the individual devices 10 belonging to the network. Each monitored participant station 10 communicates by messages relayed by server 15. A server based architecture benefits from more flexible communication options such as being able to send messages from a background process running on the mobile device without requiring user involvement at the time of sending. Message sending is typically more restricted when relying on SMS or email transmissions. A further advantage of the server based architecture is the opportunity it provides for maintaining a central database for the group. For example each member device in the group can send periodic status update packets to the server. This allows other member devices or an authorized user on a web browser to check the current status of all the group members. Server 15 may act as a collection point for logging activity reports from the multiple monitored devices 10. The server function may operate in the cloud or it may even be performed by one of the user's devices such as his or her smart phone.

Figure 2:
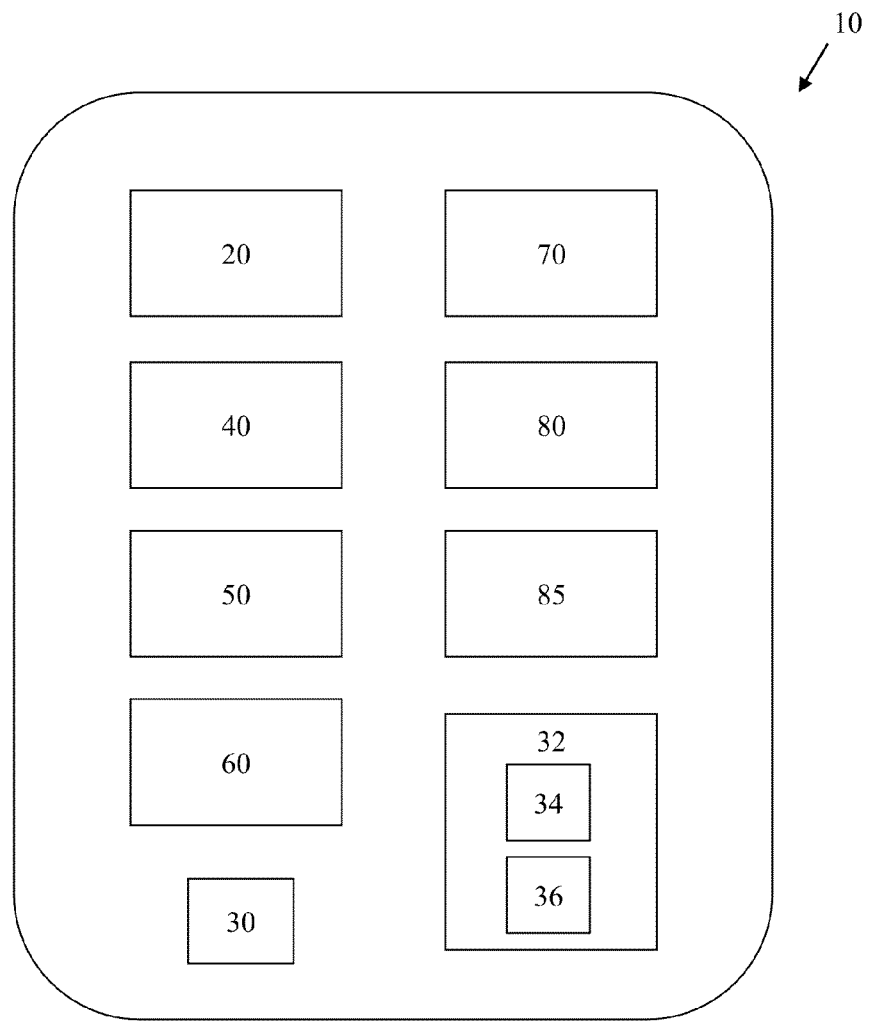
FIG. 2 illustrates the physical components of one of the participant stations in the network.

FIG. 2 illustrates the physical components of one of the participant stations (in this case a monitored smart phone) in the network, as follows.

Participant station 10 (which may be a monitored smart phone, as shown) includes a communication system 20 through which messages are transmitted to the other participant stations 10 in the network 5. Participant station 10 also includes one or both of: a GPS 30 for determining the location of the participant station, or a movement sensor 32 for detecting movement of the participant station. Movement sensor 32 may optionally include an accelerometer 34 or a gyroscope 36 or a compass or magnetic field sensor that detects changes in the orientation of the participant station (i.e.: changes in the direction the smart phone is facing).

Participant station 10 also includes a movement recording system 40 that records one or both of the location or movement of the participating station over time. For example, when participant station 10 is a smart phone, movement recording system 40 may record the movement of participant station 10 by data provided from GPS 30 as the location of the participant station changes (e.g.: as the user caries their smart phone around). Alternatively, movement recording system 40 may record the change in orientation of participant station 10 by data provided from the accelerometer 34 or gyroscope 36 of movement sensor 32 as the cell phone is handled by a user. It is to be understood that movement recording system 40 may be physical hardware on the participant station, software in the participant station, remote hardware or software, or some combination thereof.

Participant station 10 also includes an activity level measuring system 50 that measures an activity level of participating station 10 over intervals of time based on changes in one or both of the location or movement of the participant station over or between those intervals of time (e.g.: with GPS 30 determining changes in location and accelerometer 34/gyroscope 36 detecting positional movement—i.e.: changes in the direction the smart phone 10 is pointing). In preferred approaches, the activity level measuring system 50 simply turns on and operates at discrete intervals of time to detect whether the participant station has been moved a distance sufficient for GPS 30 to detect such movement or has been handled by the user (such that changes in the direction the device is pointing or facing can be detected by accelerometer 34 or gyroscope 36). As such, activity level measuring system 50 could calculate the activity level by determining the distance participant station 10 has moved in a predetermined interval of time. Or, activity level measuring system 50 could instead calculate the activity level by determining how frequently participant station 10 has moved or changed orientation within a predetermined interval of time. Preferably, activity level measuring system 50 pauses or deactivates when the smart phone is charging or when an operator is using voice or data capabilities of the smart phone. Alternatively, activity level measuring system 50 could instead increase the period of time in which activity is detected when the device is plugged in. For example, the activity level measuring system 50 could pause detection for 8 hours when the smart phone is first plugged in (assuming the user has plugged it in to charge overnight and is now sleeping). However, after 8 hours of plugged-in inactivity, the activity level measuring system 50 could restart and look for motion. This would be helpful in the case where the user has a medical emergency during the night and is not able to unplug the phone.

Participant station 10 also includes a movement threshold level identifier 60 that identifies when the activity level has remained below a pre-determined threshold for a pre-determined period of time. It is to be understood that movement threshold identifier 60 may be physical hardware on the participant station, software in the participant station, remote hardware or software, or some combination thereof.

Participant station 10 also includes an alert system 70 that transmits a message through communication system 20 to other participant stations 10 across network 5 when the movement threshold level identifier 60 has determined that the activity level has remained below the pre-determined threshold for the pre-determined period of time.

The present invention additionally provides a system where the activity level monitoring system simply acts as an activity level reporting system that transmits a message reporting the activity level through the communication system to other participant stations. This option may be carried out with a centralized server or reporting station 15, wherein each of the participant stations report their activity levels to the centralized reporting station. Optionally, these activity levels can even be reported as pedometer clicks. In this scenario, all of the network participants would receive detailed information as to how far each other walked during the course of the day. This may be very helpful when the members of the network are trying to encourage one another to remain active.

Thus, if one person in the network group becomes too sedentary, other members of the group are informed and can contact and encourage the sedentary member to increase his/her physical activity levels.

The movement recording system 40, activity level measuring system 50 and movement threshold level identifier 60 are preferably all resident in each smart phone in the network. However, it is to be understood that these components can be at separate physical locations. The communication line may be a cellular phone line or an internet communication line or other suitable communication line.

Optionally, an inquiry system 80 and a message shut off system 85 may be included as a "fail-safe" or "false alarm" system as well. Inquiry system 80 transmits a status acknowledgement message to the operator of participant station 10 prior to alert system 70 transmitting a message to other participant stations 10 in the network. For example, the message sent to the device's user may be a text or voicemail saying "Are you alright?" As will be further explained below, the status acknowledgement message encourages an operator to interact with the participant station. Once the user responds to this message, then message shut off system 85 will prevents alert system 70 from transmitting a message to other participant stations in the network. Optionally, this status acknowledgement message may be sent at irregular intervals of time. This is because messages sent at regular intervals of time may be perceived as annoying, whereas messages that tend to "surprise" the user at irregular intervals may be better received.

In optional embodiments, alert system 70 may transmit messages through the communication system to other participant stations in the network one at a time. In other words, rather than alerting all (or many) members of the network that one participant station's activity level has fallen, the various participant stations in the network may be alerted sequentially in a preferred order. For example, a neighbor may be alerted first, and (if that neighbor does not check in quickly with the user), the user's adult child may next be notified, etc.

In one optional aspect of the invention, the operator of a participant station, in response to a status acknowledgement message, may respond with a spoken command such as "I'm ok" or "Help". In the latter case, the participant station can respond with a message such as "What's wrong" and then record any spoken response from the operator. This response might be something like: "I'm sick" or "I have fallen and can't get up" and that recorded message may be sent directly to other participants in the network. In another variation of this aspect, the participant station may record ambient sound to include with its alert message to other participants in the network. This may at times capture useful sounds such as moans.

After one of the participant stations has acknowledged receiving this message, the alert system 70 can stop transmitting messages to other participant stations in the network. In this situation, the participant station which first acknowledged receiving the alert message can be the participant station that assumes responsibility to check in on the participant with the low activity level. In the example above, if the neighbor checks in with the user, then the user's adult child need not be alerted.

As will also be explained below, the status acknowledgement message preferably is not sent to the user during periods of expected low activity levels (i.e.: during times when the periods of low activity levels correspond to times or places where the participant station previously had low activity levels). For example, status acknowledge messages need not be sent during times the user is expected to be asleep, or during times when the user's GPS shows that they're in known locations such as church, at the movies or at a sporting event (and are not expected to move around much at all).

(c) Software and User Interface Design

Figure 3:
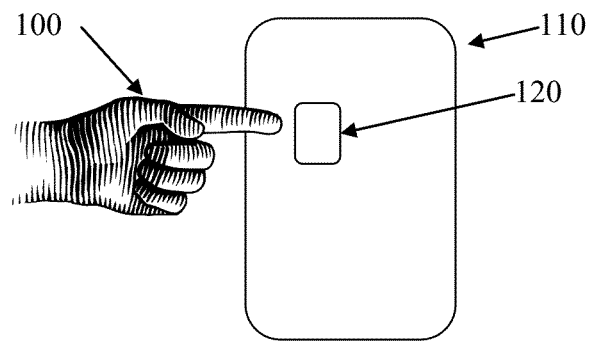
FIG. 3 illustrates the installation of software that facilitates the operation of the present invention on a mobile device.
Figure 4A:
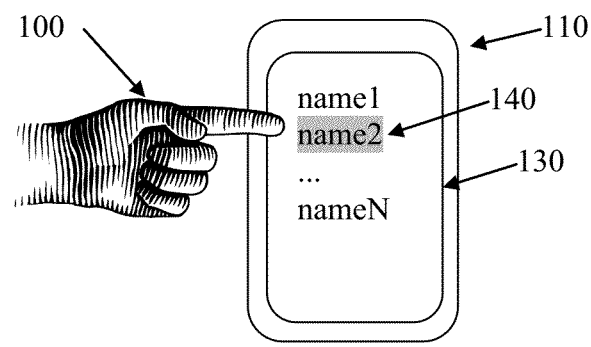
FIG. 4A illustrates a user inviting other persons to join the participant station mutual welfare monitoring network.
Figure 4B:
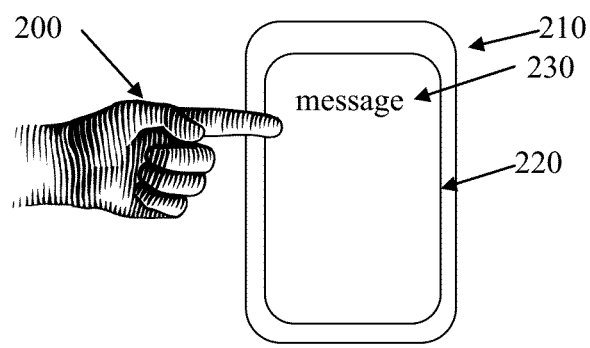
FIG. 4B illustrates a second user receiving the invitation to join the participant station mutual welfare monitoring network.
Figure 4C:
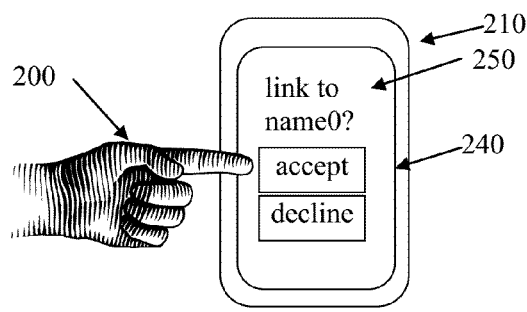
FIG. 4C illustrates the second user accepting the invitation to join a mutual welfare monitoring network.

FIG. 3 illustrates an embodiment of a first step in the formation of a mutual welfare monitoring network. A first user 100 installs a mutual welfare monitoring software application 120 on a mobile device 110. In FIG. 4A, the first user 100 activates the application 130 and selects at least one contact 140 to invite to join the network with first user 100. The application 130 sends a message to contact 140 which contains information about the application and contact information for first user 100. In FIG. 4B, the user 200 receives the sent message 230 on a message receiving application 220 which contains a means for installing application 120 on device 210 of user 200. In one embodiment, a link in an email message facilitates installing application 120. In FIG. 4C, user 200 starts the installed application 240 and is presented with a request to create a mutual monitoring network with first user 100 identified by message 250. If user 200 accepts the request 250, a message is sent back to the device 110 of user 100 and the installed application 130 on device 110 begins background activity level monitoring for user 100 with contact information for user 200 stored for use in reporting activity level alerts. Likewise, the installed application 240 begins background welfare monitoring for user 200 with contact information for user 100 stored for use in reporting low activity level alerts.

Figure 5:
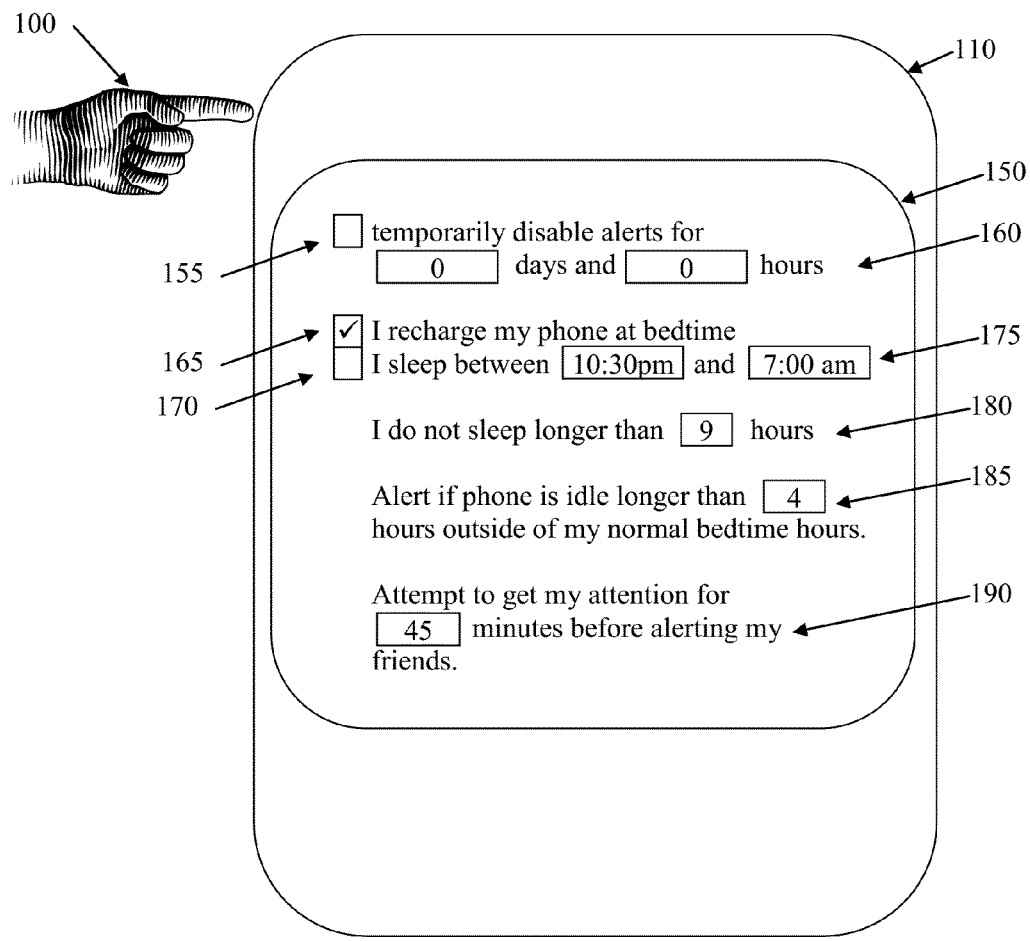
FIG. 5 illustrates a preferred settings display interface for the mutual welfare monitoring network operating on a smart phone participant station.

FIG. 5 illustrates a preferred embodiment of a settings configuration display 150. Configuration display 150 comprises a field for disabling alerts 155 for a fixed interval of time 160 as might be required if the user 100 knows the device will be idle for an extended period. Also provided is a field for specifying the user's bed time hours 165 wherein a checkbox indicates whether or not the user charges the device 110 at bedtime. An alternate field 170 explicitly sets the time interval 175 when the user sleeps. A field 180 for setting a limit on how long the user sleeps each day is included, whereby the application can signal an alert even if the device 110 remains plugged in charging for too long a time as might happen if the user 100 experiences a medical event while sleeping. A field 185 is provided for specifying how long the device 110 can remain without physical manipulation prior to signaling an alert when user is not supposed to be sleeping. A field 190 is provided for specifying how long the application should attempt to get the attention of user 100 prior to attempting to contact one or more other group members 200.

Figure 6:
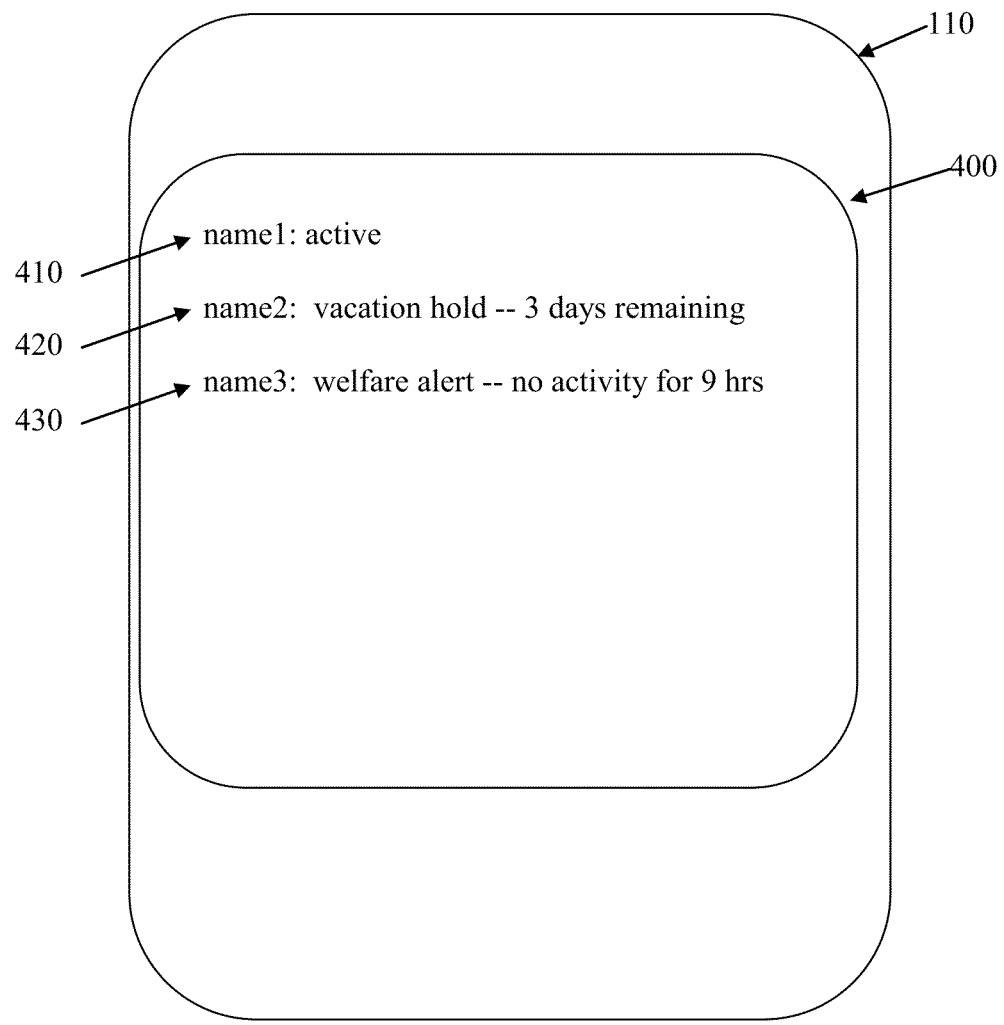
FIG. 6 illustrates a preferred status display of the mutual welfare monitoring network operating on a smart phone participant station.

FIG. 6 illustrates a preferred embodiment of an application status display 400. In this example three other users are linked with user 100. Fields 410, 420, and 430 show the status of these three users. Field 410 indicates a normal status using the term "active" in this embodiment. Field 420 shows a user whose status has been set to disable alerts. Field 430 shows a user whose application has triggered a welfare alert state. It is to be understood that other terms or icons could instead be used to indicate the different status states shown here. It is also to be understood that while this example shows three linked users with particular states, any number of linked users can be different and the states of each user will vary depending on their situations.

Figure 7:
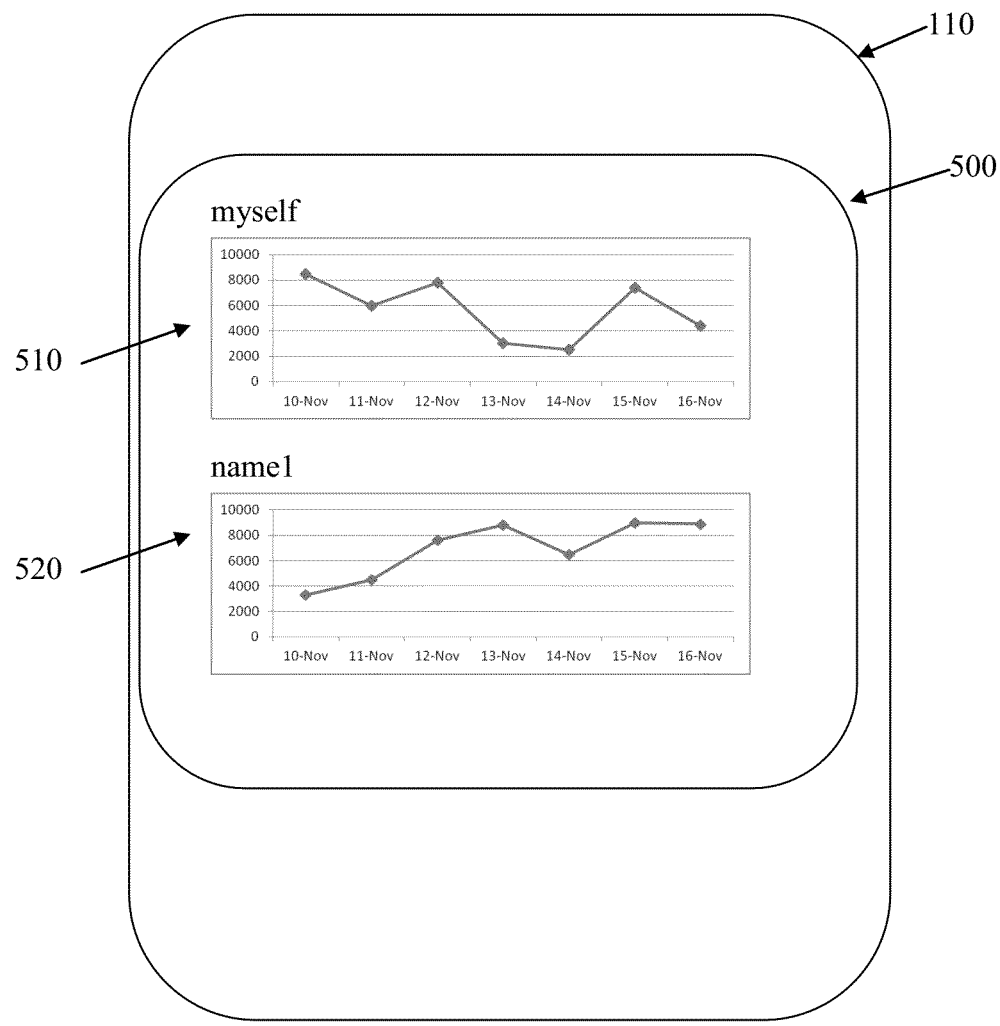
FIG. 7 illustrates an optional status display of the mutual welfare monitoring operating on a smart phone participant station.

FIG. 7 illustrates a preferred additional status display 500. In addition to providing emergency activity level monitoring, it is possible to provide each user in a group with ongoing activity measurements such as daily pedometer counts. This figure shows an example where the pedometer counts of the owner 100 for the past week are shown at 510 and the pedometer counts from a single other group member are shown at 520. This additional information can be made available to other group members as part of the application's settings panel 150. This comparative presentation of pedometer data benefits each user in the network by creating an incentive to keep up one's personal performance. It also benefits a welfare monitoring objective by providing each member with some metrical information of the other group members physical activity level which could help identify a declining health situation before an emergency occurs. It is to be understood that there may be a different number of linked users shown in this status display. It is to be further understood that there are many different ways that metrical activity levels can be displayed on a mobile device screen or on a web page.

Figure 8:
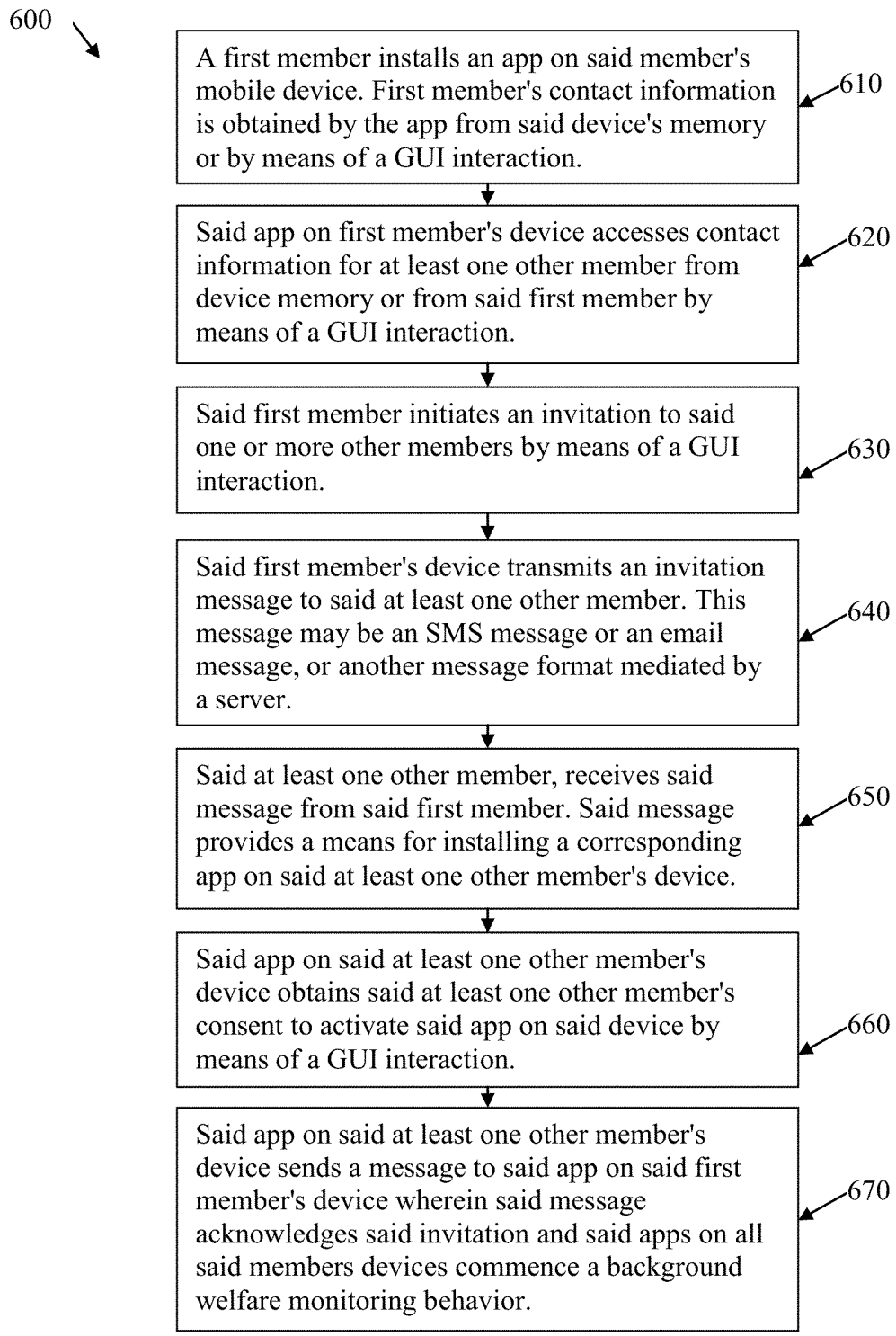
FIG. 8 illustrates a flow chart of a method for setting up a mutual welfare monitoring network among a number of inter-reporting participant stations.

FIG. 8 illustrates a method 600 for establishing a mutual welfare activity level monitoring network. At step 610 a first member installs an application on a mobile device and allows the application to acquire the first member's contact information. This contact information being comprised of at least one of the user's name or identifier information for the mobile device such as its phone number. At step 620 the user operates the application to specify at least one external contact to be invited to form a welfare monitoring network. In a preferred embodiment this contact is selected from a list of contacts obtained from the mobile device's contact directory. At step 630 the first member initiates the sending of invitations to the selected other members by a GUI interactions such as touching a button on the screen. At step 640, the application on the first member's device initiates the transmission of a message to the selected other members. In a preferred embodiment this transmission employs the SMS messaging function on the mobile device. In another embodiment this employs the email function on the mobile device. At step 650 each of the other members receives the sent message. That message identifier provides information for the first member and information about the network application and how to install it. In a preferred embodiment the message contains a link to facilitate the installation of the application. At step 660 the other users accept or decline the invitation to join the network through a GUI interaction. If the other user accepts the invitation, at step 670 the acceptance is communicated back to the first member's device along with identification information for the accepting user. At this point the first user's application begins a background monitoring process that has the accepting user as a member to contact should a welfare alert be generated. Likewise the application of the accepting member begins a background monitoring process that has the inviting user as a member to contact should a welfare alert be generated.

Figure 9:
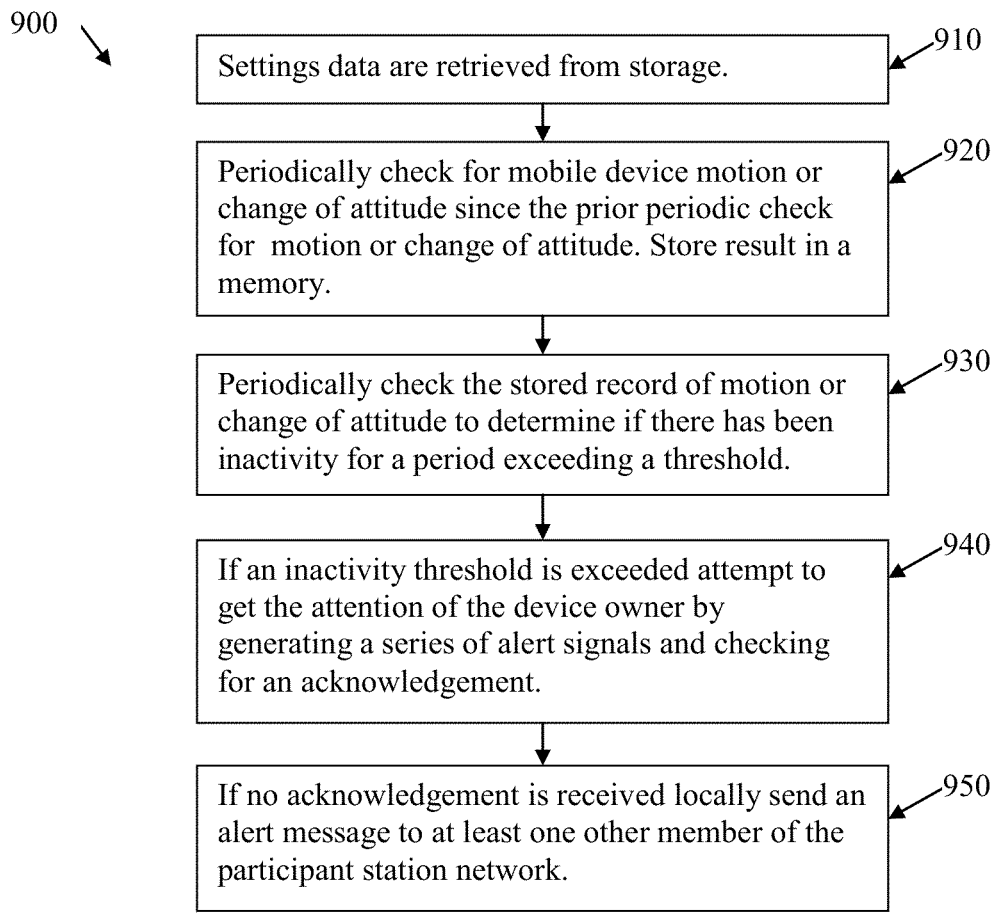
FIG. 9 illustrates flow chart of a method for activity monitoring over a mutual welfare monitoring network.

FIG. 9 illustrates one preferred method 900 for monitoring on a mobile device to detect intervals of inactivity and to generate various alerts. Unless explicitly stated, the method described herein is not constrained to a particular order or sequence. Additionally, some of the described method embodiments and elements thereof can occur or be performed at the same point in time. Method embodiments can be performed by computer executable instructions on software and/or firmware.

At step 910 user configurable settings data are retrieved.

At step 920 periodic checks are made to determine if the monitored host device has been moved since the prior periodic check. In a preferred embodiment this check is accomplished by a system call to a capability on the mobile device for logging pedometer counts or jogging or running counts. In an alternate embodiment, this is accomplished by checking for a change in the accelerometer or gyroscope readings since the prior check to determine if the physical pose of the mobile device has changed significantly. In an additional embodiment a comparison of physical location estimates is done employing such location reporting resources available on the mobile device. Such location reporting resources may include GPS, cellular radio, WI-FI, and Bluetooth based location estimation techniques as are known in art. It is to be understood that there are many means for detecting the occurrence of physical activity from one point in time to another known in the art and that these may be used individually or in combination as allowed by the capabilities of individual mobile devices. The change indications between periodic checks are logged to a memory that maintains change indication records for at least a time interval corresponding to the threshold interval for triggering a welfare alert.

At step 930 periodic checks are made to determine if there has been inactivity for a period longer than a threshold time interval that takes into account intervals when inactivity is expected such as the owner's expected bed times. In a preferred embodiment, this time interval is a settable parameter 185 and is further modified by the time of day to allow for times when the user is expected to be inactive.

If the threshold time period for low activity level is exceeded, an alert state is entered. At step 940 a first attempt is made to signal the device owner. In a preferred embodiment this attempt begins with a voice notification. In a preferred embodiment this voice notification asks the owner to pick up the mobile device as a means for acknowledging that all is well. In a preferred embodiment this attempt to alert the owner is repeated for a predetermined number of minutes. In one embodiment the repeated attempts to alert the owner utilize progressively louder sound signals.

At step 950 if no acknowledgement is received from the device owner a message is sent to at least one other member of the owner's participant station network. In a preferred embodiment this message arrives at the other member's mobile device as a SMS message. In another embodiment it arrives as a phone call with a voice message. The communicated message includes sufficient information to identify the sending device and the reason for the alert.

(d) The Preferred Motion Detection Sensors

The present invention's detection of inactivity can employ multiple systems, sensors or approaches. In one approach, motion sensing is accomplished by taking readings from the device's motion sensing components such as accelerometer 34 and gyroscope 36.

In another embodiment, periodic querying of geo-location services such as GPS 30 and wifi-location detection can indicate activity on the part of the user. A dynamic threshold for distance travelled is preferably set, taking into account the precision of the readings ensures that noisy GPS signals do not conceal lack of activity on the part of the user.

In another embodiment, activities such as turning on the device or plugging the device into a charger or unplugging it from a charger are logged as indications of activity.

On phones where continuous logging of motion in the background is not feasible due to power usage constraints, the accelerometer and/or compass outputs can be logged just occasionally, for example once every hour, and significant changes occurring from one log entry to the next would indicate that the owner has handled the device during that time interval.

In another embodiment, in addition to monitoring activity on each network members' cell phone, usage of other devices such as reading email or typing on a laptop's keyboard can also be used to augment the welfare assessment to further reduce false alarms. In this approach, the user's typing or reading emails will be logged as activity. As such, a user sitting in one place with their phone pointing in the same direction for a long period of time will still be counted as "active" if they are just reading their emails, or talking on their phone.

(e) Social Networking Functions

One novel aspect of the present invention is that its activity level monitoring function can be symmetrical among a group or network of users. Specifically, each participant station (e.g.: cell phone, laptop, etc.) in the group is monitored and an alert is sent to one or more of the other members of the group if an abnormally low activity level is detected for that participant. This aspect of the present invention addresses the needs of a wide population of single people who live alone. Such a symmetric aspect of the monitoring removes the stigma of one individual being singled out as a patient to be monitored. This makes the present invention more attractive to some elderly users who may accept being monitored by their adult children in exchange for the reciprocal ability to monitor the welfare of their adult children. This symmetric aspect augments the natural human behavior of checking up on each other in a social group. However, activity level monitoring groups need not be homogeneous (membership is not necessarily transitive). For example, a parent might enroll their neighbors and children to monitor their status; however their children might not choose to participate in monitoring the activity of their parents' friends. From time to time, members of the welfare monitoring group may drop out, permanently or temporarily (for example, because they are travelling to visit relatives and their patterns may change substantially, and their ability to respond may be compromised).

In one approach, the present system optionally identifies when a welfare monitoring network falls below a defined critical mass, and warns the user to augment their group by seeking new members.

In another approach, professional monitoring agents or services may participate in the welfare monitoring group, potentially for a fee. If no one in the group responds to an alert in a timely fashion, the professional agent can take appropriate action.

Advantageously, the present invention fosters a "set it and forget it" character for the mutual welfare activity level monitoring system. In one preferred embodiment of the invention, mutual activity level welfare monitoring may be integrated with a social network such as Google+ or Facebook. For example in the Google+ framework, the circle concept is used as an organizing mechanism for identifying different subgroups of individuals in one's social network. In a preferred embodiment, a special welfare monitoring circle would be created and reciprocated membership in this circle by a pair of users would enable the welfare monitoring system to operate. This system would be in part supported by special software on the Google+ servers and in part by special applications running on each member's mobile device. A similar integration with other social networking systems such as Facebook can be envisioned.

In optional aspects, additional devices can augment the activity level monitoring by providing additional signals of activity to the monitored user's smartphone or household PC. For example, a class of activity monitoring devices such as Smart watches (e.g. Pebble), wrist bands (Nike Up), and potential future devices that are carried or worn, such as smart key-rings, smart wallets, smart clothing, exercise devices or equipment and the like can be used. These devices can be networked or connected via Bluetooth or similar local wireless networks. Data provided from these monitored devices can be used to show that the user is indeed active (even when not using their activity level monitored smart phone). This mitigates the risk that the system learns an infrequent movement pattern for a user who does not carry their smartphone at all times and thereby delays detecting a real incident where the user becomes incapacitated.

(f) Device Personalization

In order for the present invention to perform optimally, each member of the network must interact with their monitored device on a regular basis. Otherwise, the time threshold for triggering an inactivity alarm would have to be set very long, making the device less responsive to real emergencies. While some individuals carry their mobile device at all times, others may leave their mobile device unattended for extended periods which would compromise our ability to measure inactivity reliably.

Therefore, in one aspect of the present invention, a system is provided for encouraging increased interaction without creating a nuisance for the user. In this system, the monitored device behaves much like a virtual pet that returns some reinforcing feedback to the owner when the device is handled after extended inattention. For example, an audible chirp, a brief vibration with a simple pattern that resembles a wink or a purr, or a spoken phrase like "thanks" in a pleasant voice with a configurable gender (possibly opposite the gender of the owner) is provided. The particular acknowledgement used could also vary from time to time to create the illusion of some intelligence in the device.

Using this approach, when the device is left unattended for a time nearing the warning threshold, an alarm might be sounded, with the monitored mobile device then executing a series of audible sounds, progressing from a gentle sound like a small chirp on to louder sounds or spoken requests spaced out over intervals of time and ending with more dire announcements asking the owner to please handle the device. This sequence might extend over several hours—a period that would be user configurable or automatically adjusted based on the owner's prior interaction history. When the device owner finally does respond to these calls for attention, the reinforcing feedback could be used to reduce any annoyance created by the request for attention. It is anticipated that over time the owner will become somewhat trained by the device, and give the device more regular attention.

In a preferred approach, the present device learn from past owner behavior so a longer inactivity interval would be used at first, but as the owner becomes accustomed to "caring for" the device, and the interaction history shows fewer long gaps, and the alarm threshold time could be shortened. This interactive behavior, generating requests for attention and returning simple acknowledgements when handled could enhance the reliability of the present activity level background monitoring function.

To further enhance reliability of the inactivity monitoring function, the present system could also monitor the charge state of the mobile device and generate an audible request to be plugged in when the charge is getting low. The request and acknowledgement sounds could be made in a way consistent with a virtual pet to maintain the illusion of an animate personality in the device.

False alarms are not desirable, and there are situations where a member of a mutual activity level monitoring network would want to inhibit the operation of the activity monitor. Described herein is a control panel setting for setting a vacation hold mode. However, for more routine situations such as going to the gym for a long workout it could be an encumbrance for the owner to have to remember to set the monitor in a hold mode before storing the mobile device in a locker.

Therefore, yet another approach is to place the device into a particular physical attitude or orientation. For example, the device could be placed so that it leans against a vertical wall with its top edge down and its bottom edge up and resting against the vertical surface. This unusual pose would signal the activity monitoring sensor that the owner desires activity monitoring to be temporarily suspended. Activity level monitoring could last until the device is moved out of this upside down pose. Optionally, the inactivity hold off could be extended for example for 12 hours, but then it would activate after that period if no activity is sensed. While the upside down physical orientation described above could occur at other times such as when in the owner's pocket, these cases can be distinguished from those where the owner intents to signal an extended hold, by the detection of motion during the time that the device is in the said unusual orientation.

In addition, when a user goes to bed, the system could adjust the inactivity time threshold to cover the night time period when the owner is likely to be sleeping and/or detect when the mobile device is plugged in for charging. However, in other situations like these, the present system can infer that the inactivity time threshold should be lengthened. For example, such an inference can be made by checking whether the device is away from the owner's home location. This can be determined in a number of ways, for example through a GPS location check or by means of Wi-Fi connectivity to the home network. If the device is determined to be away from the home location, a different alarm time threshold can be set. Another approach is to allow the owner to use a voice command to activate a hold mode. For example, on an Apple device, the Siri interface might be employed to streamline control of the welfare monitoring application.

Once the owner has indicated that a longer hold off is desired, a preferred embodiment would associate that request with the current location of the device. This can be established using GPS, Wi-Fi, or another location estimation mechanism. That location can be stored in a memory for future use. For example, if in the future, an inactivity alarm timeout is nearing, the device's location can be compared with these prior stored locations. If the device is close to one of them and it is not close to the home location, which is treated as a special case, a longer time interval can be employed.

A history of inactivity associated with locations can also be stored in memory so that the alarm interval can be automatically adapted based on prior experience at a given location. Thus if the owner frequents a location where the device is left untouched for long periods of time, the monitoring program can adjust its inactivity alarm interval to take that historical behavior into account and avoid generating false alarms.

What is claimed is:

1. A network of interreporting participant stations configured to monitor and analyze station movement such that activity levels of each of the individual participant stations can be determined and reported across the network to each of the other individual participant stations in the network such that each individual participant station both transmits its own activity level to each of the other individual participant stations in the network and receives the activity levels of each of the other individual participant stations in the network, comprising:
a plurality of participant stations, each participant station comprising:
  (a) a communication system enabling message transmission to each of the other participant stations in the network;
  (b) one or both of:
    (i) a GPS for determining a location of the participant station, or
    (ii) a movement sensor for detecting movement of the participant station;
  (c) a movement recording system that activates at periodic intervals of time to record one or both of the location or movement of the participating station at each of the periodic intervals of time;
  (d) an activity level measuring system that measures an activity level of the participating station by detecting changes in one or both of the location or movement of the participant station occurring between each of the periodic intervals of time;
  (e) a movement threshold level identifier that identifies when the activity level has remained below a pre-determined threshold for a pre-determined period of time, wherein the pre-determined period of time is greater than each of the periodic intervals of time;
  (f) an alert system that transmits a message through the communication system to the other participant stations in the network when the movement threshold level identifier has determined that the activity level has remained below the pre-determined threshold for the pre-determined period of time; and
  (g) an inquiry system that transmits a status acknowledgement message to an operator of the participant station prior to the alert system transmitting a message to each of the other participant stations in the network; and
  (h) a message shut off system that prevents the alert system from transmitting a message to each of the other participant stations in the network if the operator responds to the status acknowledgement message sent by the inquiry system, and
wherein the status acknowledgement message is not sent during periods of low activity level when the periods of low activity level correspond to times when or places where the participant station previously had low activity level.

2. The network of claim 1, wherein the movement sensor comprises an accelerometer in the participant station.

3. The network of claim 1, wherein the movement sensor detects changes in an orientation of the participant station.

4. The network of claim 1, wherein the activity level measuring system calculates the activity level by determining a distance the participant station has moved in a predetermined interval of time.

5. The network of claim 1, wherein the activity level measuring system calculates the activity level by determining how frequently the participant station has changed orientation in a predetermined interval of time.

6. The network of claim 1, wherein each of the plurality of participant stations are smart phones.

7. The network of claim 6, wherein the movement recording system and the activity level measuring system and the movement threshold level identifier are all resident in each smart phone in the network.

8. The network of claim 6, wherein the activity level measuring system changes the interval of time at which the activity level is measured when the smart phone is charging or an operator is using voice or data capabilities of the smart phone.

9. The network of claim 6, wherein the activity level measuring system changes the interval of time at which the activity level is measured when the smart phone is placed in an unusual attitude.

10. The network of claim 1, wherein the communication system comprises a cellular phone line or an internet communication line.

11. The network of claim 1, wherein the activity level measuring system activates and determines the activity level only at periodic intervals of time.

12. The network of claim 1, wherein the operator of the participant station responds to the status acknowledgement message by voice command.

13. The network of claim 12, further comprising:
(i) an audio messaging system that adds an operator-recorded message to the message transmitted by the alert system to the other participant stations in the network.

14. The network of claim 1, wherein the alert system transmits messages through the communication system to each of the other participant stations in the network, and wherein the alert system stops transmitting messages to each of the other participant stations in the network after one of the other participant stations has acknowledged receipt of the message.

15. The network of claim 1, wherein the status acknowledgement message is sent at irregular intervals of time.

16. The network of claim 1, wherein the status acknowledgement message encourages the operator to interact with the participant station.

17. A network of interreporting participant stations configured to monitor and analyze station movement such that activity levels of each of the individual participant stations can be determined and reported across the network to each of the other individual participant stations in the network such that each individual participant station both transmits its own activity level to each of the other individual participant stations in the network and receives the activity levels of each of the other individual participant stations in the network, comprising:

a plurality of participant stations, each participant station comprising:
(a) a communication system enabling message transmission to each of the other participant stations in the network;
(b) one or both of:
 (i) a GPS for determining a location of the participant station, or
 (ii) a movement sensor for detecting movement of the participant station;
(c) a movement recording system that activates at periodic intervals of time to record one or both of the location or movement of the participating station at each of the periodic intervals of time;
(d) an activity level measuring system that measures an activity level of the participating station by detecting changes in one or both of the location or movement of the participant station occurring between each of the periodic intervals of time;
(e) a movement threshold level identifier that identifies when the activity level has remained below a pre-determined threshold for a pre-determined period of time, wherein the pre-determined period of time is greater than each of the periodic intervals of time; and
(f) an alert system that transmits a message through the communication system to the other participant stations in the network when the movement threshold level identifier has determined that the activity level has remained below the pre-determined threshold for the pre-determined period of time;
wherein each of the plurality of participant stations are smart phones
wherein the activity level measuring system changes the interval of time at which the activity level is measured when the smart phone is placed in an unusual attitude, and,
wherein the unusual attitude is the smart phone resting on its top edge leaning against an object.

* * * * *